(12) United States Patent
Gall

(10) Patent No.: US 6,596,745 B2
(45) Date of Patent: Jul. 22, 2003

(54) METHOD FOR TREATING FIBROTIC DISEASES WITH AZOLIUM CHROMAN COMPOUNDS

(75) Inventor: Martin Gall, Morristown, NJ (US)

(73) Assignee: Alteon, Inc., Ramsey, NJ (US)

( * ) Notice: Subject to any disclaimer, the term of this patent is extended or adjusted under 35 U.S.C. 154(b) by 0 days.

(21) Appl. No.: 10/158,344

(22) Filed: May 30, 2002

(65) Prior Publication Data

US 2003/0004194 A1 Jan. 2, 2003

Related U.S. Application Data

(60) Provisional application No. 60/294,438, filed on May 30, 2001.

(51) Int. Cl.$^7$ .................. A61K 31/427; A61K 31/38
(52) U.S. Cl. ............. 514/365; 514/227.8; 514/233.5; 514/236.8; 514/241; 514/247; 514/252.13; 514/252.14; 514/253.09; 514/253.1; 514/253.13; 514/254.01; 514/254.02; 514/254.05; 514/254.11; 514/314; 514/326; 514/342; 514/367; 514/397; 514/399; 514/402; 514/438; 514/439; 514/442; 514/443; 514/444; 514/456; 514/824; 514/838; 514/851; 514/866; 514/878
(58) Field of Search .................. 514/365, 227.8, 514/236.8, 314, 326, 342, 367, 233.5, 241, 247, 252.13, 252.14, 253.09, 253.1, 253.13, 254.01, 254.02, 254.05, 254.11, 397, 399, 402, 438, 439, 442, 443, 444, 456

(56) References Cited

U.S. PATENT DOCUMENTS 5,853,703 A * 12/1998 Cerami et al. ................ 424/53
6,121,300 A * 9/2000 Wagle et al. ............... 514/365

FOREIGN PATENT DOCUMENTS

JP        07033767     2/1995
WO     WO 87/05020    8/1987

* cited by examiner

Primary Examiner—Frederick Krass
(74) Attorney, Agent, or Firm—Dechert

(57) ABSTRACT

Provided is a method of treating or ameliorating hypertension in an animal comprising administering an effective amount of a compound of formula I:

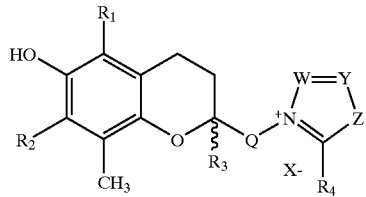

28 Claims, No Drawings

METHOD FOR TREATING FIBROTIC DISEASES WITH AZOLIUM CHROMAN COMPOUNDS

This application claims the priority of U.S. Application No. 60/294,438, filed May 30, 2001.

The present invention relates to methods for treating certain fibrotic diseases or other indications.

Glucose and other sugars react with proteins by a non-enzymatic, post-translational modification process called non-enzymatic glycosylation. At least a portion of the resulting sugar-derived adducts, called advanced glycosylation end products (AGEs), mature to a molecular species that is very reactive, and can readily bind to amino groups on adjacent proteins, resulting in the formation of AGE cross-links between proteins. Recently a number of classes of compounds have been identified whose members inhibit the formation of the cross-links, or in some cases break the cross-links. These compounds include, for example, the thiazolium compounds described in U.S. Pat. No. 5,853,703. As AGEs, and particularly the resulting cross-links, are linked to several degradations in body function linked with diabetes or age, these compounds have been used, with success, in animal models for such indications. These indications include loss of elasticity in blood vasculature, loss of kidney function and retinopathy.

Now, as part of studies on these compounds, it has been identified that these compounds inhibit the formation of bioactive agents, such as growth factors and inflammatory mediators, that are associated with a number of indications. These agents include vascular endothelial growth factor (VEGF) and TGF[beta]. As a result, a number of new indications have been identified for treatment with agents that inhibit the formation of, or more preferably break, AGE-mediated cross-links. It is not unreasonable to infer that the effects seen are due to the removal of AGE-related molecules that provide a stimulus for the production or release of these growth factors. Removal of such molecules is believed to proceed in part due to the elimination of AGE-related cross-links that lock the AGE-modified proteins in place. Moreover, such compounds also reduce the expression of collagen in conditions associated with excess collagen production. Regardless of the mechanism, now provided are new methods of treating a number of indications.

SUMMARY OF THE INVENTION

In one embodiment, the invention relates to a method of treating or ameliorating or preventing an indication of the invention in an animal, including a human, comprising administering an effective amount of a compound of the formula I:

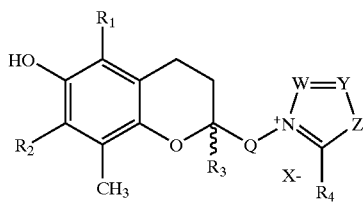

wherein: W and Y are independently N or, respectively, $CR^W$ or $CR^Y$. Z is O, S or $NR^Z$. Q is —$CH_2$— or —(CO)—$CH_2$—, where the methylene is bonded to a ring nitrogen. $R^W$ and $R^Y$ are independently hydrogen, alkyl, —C≡$CR^E$, —$CH_2$—C≡$CR^P$, alkenyl, aryl, arylalkyl, aryloxy, arylthio, amino, alkylamino, arylamino, dialkylamino, diarylamino, $CH_3C(O)NH$—, fluoroalkyl, perfluoroaryl, hydroxyalkyl, $C(O)NH_2$, and $S(O)_2NH_2$ or, together with their ring carbon atoms form a fused 6-membered aromatic or heteroaromatic ring, wherein $R^E$ or $R^P$ is alkyl, hydrogen, hydroxyalkyl or aryl. $R^Z$ is alkyl, —$CH_2$—C≡$CR^P$, aryl, arylalkyl, or aroylalkyl. $R^1$ and $R^2$ are independently hydrogen, alkyl or hydroxymethyl. $R^3$ is hydrogen or methyl. $R^4$ is acetamido, hydrogen, methyl, amino, —C≡$CR^E$, —$CH_2$—C≡—$CR^P$ alkylthio, fluoromethyl, difluoromethyl, trifluoromethyl, cyanomethyl, hydroxyalkyl, alkoxycarbonyl-methyl, 1-(alkoxycarbonyl)-1-hydroxyalkyl or aminocarbonylmethyl. (The "1" notations of "1-(alkoxycarbonyl)-1-hydroxyalkyl" indicates that a terminal methyl [but for the recited substitutions] of "alkyl" is substituted with the hydroxyl and esterified carbonyl.)

DETAILED DESCRIPTION OF THE INVENTION

Certain Fibrotic Diseases

Among the indications that can be treated with the invention are a number of indications linked to or associated with the formation of excess collagen. Among these, a number of the indications can be termed fibrotic diseases.

Such fibrotic diseases include systemic sclerosis, mixed connective tissue disease, fibrodysplasia, fibrocystic disease, sarcoidosis, myositis (e.g. polymyositis, primary idiopathic polymyositis, childhood polymyositis, dermatomyositis, childhood dermatomyositis, primary idiopathic dermatomyositis in adults, inclusion body myositis, polymyositis or dermatomyositis associated with malignant tumors). Dermatomyositis can be associated with fibrosing or hypertrophic aspects, including fibrosing alveolitis and pulmonary fibrosis. Treatment using the invention is expected to treat, prevent, reduce or ameliorate such diseases or hypertrophy, fibrotic hypertrophy or fibrosis in such diseases. Amelioration includes reducing the rate of progression of a disease.

Among these fibrotic diseases are diseases that have as a manifestation fibrotic vascular intimal hypertrophy. These diseases include vasculitis (including coronary artery vasculitis), polyarteritis nodosa or temporal arteritis. Treatment using the invention is expected to treat, prevent, reduce or ameliorate vascular intimal hypertrophy in such diseases.

These fibrotic diseases further include diseases that have as a manifestation fibrotic hypertrophy of skin and/or muscle tissue. These diseases include scleroderma, eosinophilic fasciitis, discoid lesions associated with lupus or discoid lupus or surgical adhesions. Treatment using the invention is expected to treat, prevent, reduce or ameliorate such indications or hypertrophy or fibrosis of skin or muscle tissue.

Such fibrotic diseases further include diseases that have as a manifestation fibrotic hypertrophy of nerve tissue. These diseases include cerebrosclerosis, annular sclerosis. diffuse sclerosis and lobar sclerosis. Treatment using the invention is expected to treat, prevent, reduce or ameliorate such diseases, or hypertrophy, fibrotic hypertrophy or fibrosis of nerve tissue in such diseases.

These fibrotic diseases further include fibrotic lung diseases that have as a manifestation fibrotic hypertrophy or fibrosis of lung tissue. These diseases include pulmonary fibrosis (or interstitial lung disease or interstitial pulmonary fibrosis), idiopathic pulmonary fibrosis, the fibrotic element of pneumoconiosis (which is associated with exposure to environmental hazards such as smoking, asbestos, cotton lint, stone dust, mine dust and other particles), pulmonary sarcoidosis, fibrosing alveolitis, the fibrotic or hypertrophic element of cystic fibrosis, chronic obstructive pulmonary disease, adult respiratory distress syndrome and emphysema. Treatment using the invention is expected to treat, prevent, reduce or ameliorate such diseases, or hypertrophy, fibrotic hypertrophy or fibrosis in such diseases.

Such fibrotic diseases further include diseases that have as a manifestation fibrotic hypertrophy or fibrosis of prostate, liver, the pleura (e.g., pleurisy, pleural fibrosis) or pancreas. These diseases include benign prostatic hypertrophy (BPH) and fibrosis of the liver. Treatment using the invention is expected to treat, prevent, reduce or ameliorate such diseases, or hypertrophy, fibrotic hypertrophy or fibrosis in such diseases.

These fibrotic diseases further include diseases that have as a manifestation fibrotic hypertrophy or fibrosis of the bowel wall, such as inflammatory bowel disease, including Crohn's disease. Treatment using the invention is expected to treat, prevent, reduce or ameliorate such diseases, or hypertrophy, fibrotic hypertrophy or fibrosis in such diseases.

Arteriosclerosis, Atherosclerosis, Stiff Vessel Disease, Peripheral Vascular Disease, Coronary Heart Disease, Stroke, Myocardial Infarct, Cardiomyopathies, Restenosis Arteriosclerosis is a disease marked by thickening, hardening, and loss of elasticity in arterial walls, of which atherosclerosis is a sub-type. Arteriosclerosis in turn falls within the genus of stiff vessel diseases. Without limitation to theory, it is believed that damage to the blood vessels of these diseases is due to AGE-caused damage, either through protein cross-linking or the stimulation of bioactive agents, or both. Accordingly, the first agents are used to treat, prevent, reduce or ameliorate stiff vessel disease, including arteriosclerosis and athersclerosis. Peripheral vascular disease is an indication that overlaps with atherosclerosis but also covers disease which is believed to have a stronger inflammatory component. First agents are used to treat, prevent, reduce or ameliorate peripheral vascular disease. Coronary heart disease is a form of atherosclerosis of the coronary arteries. First agents are used to treat, prevent, reduce or ameliorate coronary heart disease.

When the heart pumps blood into the vascular system, the ability of the arteries to expand helps to push blood through the body. When arteries become stiff, as they do in the natural process of aging, the ability of the arteries to expand is diminished and also has consequences for the heart. The heart has to work harder to pump the blood into the stiff arteries, and eventually hypertrophies (enlarges in size) to accomplish this. A hypertrophied heart is an inefficient pump, and is one of the disorders that leads to congestive heart failure. One compound believed to work by a mechanism shared by the compounds of the invention, 3-[2-phenyl-2-oxoethyl]-4,5-dimethyl-thiazolium salt, showed an ability to reverse the stiffness of arteries in a Phase IIa clinical trial, as measured by the ratio of stroke volume (ml) to pulse pressure (mm Hg). The potential clinical benefit of this is to lessen the effort that the heart must expend to push blood throughout the body. The effect is also believed to contribute to preventing hypertrophy and subsequent inefficiency of the heart, which inefficiency would contribute to congestive heart failure.

Stroke is a cardiovascular disease that occurs when blood vessels supplying blood (oxygen and nutrients) to the brain burst or are obstructed by a blood clot or other particle. Nerve cells in the affected area of the brain die within minutes of oxygen deprivation and loss of nerve cell function is followed by loss of corresponding bodily function. Of the four main types of stroke, two are caused by blood clots or other particles. The former two are the most common forms of stroke, accounting for about 70–80 percent of all strokes.

Blood clots usually form in arteries damaged by atherosclerosis. When plaque tears from the sheer forces of blood flowing over an uneven, rigid cap atop the plaque site, thrombotic processes become involved at the "injury" site. As a result, clots can form. First agents are used to prevent, reduce or ameliorate the risk of stroke in patients who have suffered previous strokes or have otherwise been identified as at risk.

First agents can also be used to treat, prevent, reduce or ameliorate peripheral vascular disease and periarticular rigidity.

Treatment with the first agents during the relatively immediate aftermath of a heart attack can be used to reduce the size of the myocardial infarct resulting from the heart attack. This treatment is preferably administered within six hours of the heart attack, more preferably, within three hours. While the dosages discussed below can be used with this indication, such as a dose of 0.01–4.0 mg/kg administered orally or 0.01–2.0 mg/kg administered intravenously, preferably within the time period outlined above. Preferred routes of administration include i.v. injection or i.v. drip. Thereafter, optional supplemental administrations can be made with the dosages described below.

Atherosclerosis is a disease that involves deposition of blood lipids in plaque in the arteries throughout the body. In coronary arteries, accumulation of plaque progressively leads to reduced coronary flow, with occlusion of the arteries causing focal death of cardiac tissue (myocardial infarction, heart attack). If the amount of tissue that dies is large enough, death ensures. In a Phase IIa trial, one compound believed to work by a mechanism shared by the compounds of the invention, 3-[2-phenyl-2-oxoethyl]-4,5-dimethyl-thiazolium salt, increased the amount of circulating triglycerides (lipids). Consistent with the known presence of AGEs in plaque, the result indicates that the agent had a lipid mobilizing effect on arterial plaque. Reducing local deposits of plaque should eventually lessen the risk of myocardial infarction and death due to heart attacks.

Fibrotic diseases further include diseases that have as a manifestation fibrotic hypertrophy of the heart. These diseases include endomyocardial fibrosis (wherein endocardium and subendocardium are fibrosed, such as in some manifestations of restrictive cardiomyopathy), dilated congestive cardiomyopathy (a disorder of myocardial function with heart failure in which ventricular dilation and systolic dysfunction predominate), hypertrophic cardiomyopathy (characterized by marked ventricular hypertrophy with diastolic dysfunction in the absence of an afterload demand), and other cardio-hypertrophies. In dilated congestive cardiomyopathy, typically at presentation there is chronic myocardial fibrosis with diffuse loss of myocytes. In hypertrophic cardiomyopathy, usually the interventricular septum is hypertrophied more than the left ventricular posterior wall (asymmetric septal hypertrophy). Treatment using the invention is expected to treat, prevent, reduce or ameliorate such diseases, or hypertrophy, fibrotic hypertrophy or fibrosis in such diseases.

Hypertrophies of the heart can be diagnosed and monitored by methods known in the art, such as by electrocardiogram, echocardiography or magnetic resonance imaging. Such diagnostic methods can be applied in particular for subjects having a risk factor for such hypertrophy, such as congestive heart failure, prior cardiac surgery or diabetes. In one aspect, the invention comprises identifying cardio-hypertrophy with using biophysical diagnostic tools, and administering an active agent of the invention to treat, prevent, reduce or ameliorate such diseases, or hypertrophy, fibrotic hypertrophy or fibrosis in such diseases. The invention can further include monitoring cardio-hypertrophy during the course of treatment with active agent.

Erosion or tearing of arterial wall plaque can occur due to the rough and irregular shape of the plaque as it forms from deposition of lipids and invasion of cells such as monocytes and macrophages (foam cells). When erosion occurs platelets and other components of the blood clotting system are activated, resulting in formation of a clot (thrombus). When the thrombus grows to such as state that blood flow is reduced, severe angina attacks that characterize unstable angina can occur. Plaque forms irregular shapes and in doing so creates shear stresses from the flow of blood over this irregular form. It is the irregularity of plaque shape that leads to the dislodging or tearing of the plaque, and to the subsequent invasion of reactive cells. On the surface of plaque is collagen, which is believed to contribute to the rigidity of the irregular shape. Without limitation to theory, it is believed that reducing the crosslinking of such a rigid collagen cap results in smoother blood flow, with a reduced risk of angina-causing tears. Accordingly, first agents are used to treat, prevent, reduce or ameliorate unstable angina.

Faithful conduction of the electrical impulse from the sinoatrial to the atrioventricular nodes depends upon close apposition of myocardial cells. Excess production of collagen in the heart, which occurs naturally with aging but more so in diabetes and in conditions of heart disorders such as hypertension, causes an increase in the distance between myocardial cells, leading to atrial fibrillation. First agents are used to treat, prevent, reduce or ameliorate atrial fibrillation.

The fibrotic indications further include restenosis, which is the process of increasing artery closure following an operation to open the artery, such as balloon angioplasty.

Bladder Elasticity

Indications that can be treated, prevented, reduced or ameliorated with the first agents include loss of bladder elasticity. Bladder elasticity is tied to the frequency of urination, and the urgency of desire to urinate. Accordingly, the invention can be used to treat, prevent, reduce or ameliorate non-obstructive uropathy, a disorder characterized by an overactive bladder that entails increased frequency of urination, a strong and sudden desire to urinate (urgency) which may also be associated with involuntary urinary leakage (urge incontinence).

Macular Degeneration

The effect of the first agents in reducing levels of other endogenous bioactive agents, particularly VEGF and/or TGF[beta], is believed to underlie effectiveness against macular degeneration or macular edema. Again, however, the invention is not limited to theory. Moreover, a anti-fibrotic effect or another effect against tissue hypertrophy may contribute. Treatment using the invention is expected to treat, prevent, reduce or ameliorate macular degeneration. In one aspect of the invention, the treatment is used to treat, prevent, reduce or ameliorate the wet form of macular degeneration or macular edema. In the wet form, new blood vessel growth has a greater contribution to the disease.

Amyotrophic Lateral Sclerosis (ALS)

ALS is associated with degradations of the motor neuron system and/or the posterior column of the spinal cord. In ALS patients, these structures tend to stain with AGE-reactive antibodies. Treatment using the invention is expected to treat, prevent, reduce or ameliorate ALS.

Rheumatoid Arthritis, Osteoarthritis, Bone Resorption

It is believed, without limitation to such theory, that reducing AGE accumulation at the joints affected by rheumatoid arthritis or osteoarthritis reduces stimulation of the production of cytokines involved in inflammatory processes of the disease. Treatment using the invention is expected to treat, prevent, reduce or ameliorate rheumatoid arthritis or osteoarthritis. Similarly, it is believed that reducing AGE accumulation at bone reduces stimulation of bone resorption. Accordingly, the invention is used to treat, prevent, reduce or ameliorate osteorporosis, bone loss or brittle bone.

Dialysis

The first agents can be administered as part of a dialysis exchange fluid, thereby preventing, limiting or ameliorating the damage to tissue caused by the sugars found in such exchange fluid. For example, first agents are expected to prevent, limit or ameliorate the stiffening and sclerosing of peritoneal tissue that occurs in peritoneal dialysis, as well as prevent, limit or ameliorate the formation of new blood vessels in the peritoneal membrane. In hemodialysis, first agents are expected to prevent, limit or ameliorate the stiffening and sclerosing of red blood cells and vasculature resulting from exposure to the sugars exchanged into the blood during dialysis. Exchange fluids for peritoneal dialysis typically contain 10–45 g/L of reducing sugar, typically 25 g/L, which causes the formation of AGEs and consequent stiffening and degradation of peritoneal tissue. Similarly, hemodialysis fluids typically contain up to about 2.7 g/L of reducing sugar, typically 1 to 1.8 g/L. Thus, the invention provides methods by which the first agents are provided in these fluids and thereby prevent, limit or ameliorate the damage that would otherwise result. Alternatively, the invention provides methods whereby the first agents are administered by the methods described below to prevent, limit or ameliorate such damage from dialysis. In hemodialysis, the exchange fluid preferably contains 0.006–2.3 mg/L of an agent of the invention, more preferably, 0.06 to 1.0 mg/L. In peritoneal dialysis, the exchange fluid preferably contains 0.01 to 24 mg/L of an agent of the invention, or preferably, 1.0 to 10 mg/L.

In one embodiment, preventing or ameliorating is effected with a second agent. A preferred route of administration is inclusion in the dialysis fluids. In hemodialysis, the exchange fluid preferably contains 0.125 to 2.5 mg/L of aminoguanidine, more preferably, 0.2 to 1.0 mg/L. In peritoneal dialysis, the exchange fluid preferably contains 1.25 to 25 mg/L of aminoguanidine, or preferably, 2.0 to 10 mg/L. In a preferred aspect of the invention, the first agents are initially administered, and subsequently second agents are used to moderate or limit damage thereafter.

Asthma

It is believed, without limitation to such theory, that the first agents or second agents act to prevent, reduce or ameliorate the small but significant thickening of the lung airways associated with asthma. Moreover, the agents are believed to reduce stimulation of the production of cytokines involved in inflammatory processes of the disease. Accordingly, the agents are used to treat, prevent, reduce or ameliorate asthma. In this embodiment, one preferred route of administration is pulmonary, such as via an aerosol, though peroral administration is also preferred.

Carpal Tunnel Syndrome

It is believed, without limitation to such theory, that the first agents act to prevent, reduce or ameliorate fibrotic and cytokine-induced elements of carpal tunnel syndrome. Accordingly, the first agents are used to treat, prevent, reduce or ameliorate carpal tunnel syndrome.

Fibrotic diseases also include Dupuytren's contracture, a contracture of the palmar fascia often causing the ring and little fingers to bend into the palm. Treatment using the invention is expected to treat, prevent, reduce or ameliorate Dupuytren's contracture, or hypertrophy, fibrotic hypertrophy or fibrosis in Dupuytren's contracture.

In these embodiments, one preferred route of administration is local injection.

Periodontal Disease

The incidence of periodontal disease is higher in subjects with either insulin-deficient or insulin-resistant diabetes, with consequent hyperglycemia. Again, without limitation to such theory, it is believed that the first agents act to prevent, reduce or ameliorate AGE-induced cytokine action to create or exacerbate periodontal disease. Accordingly, the first or second agents are used to treat, prevent, reduce or ameliorate periodontal disease. In this embodiment, one preferred primary or supplemental route of administration is via mouthwash, or compositions adapted for delivery into the subgingival periodontal pocket (such as implants and erodible microspheres). Peroral administration is again useful. The mouthwash preferably contains 0.003–1.0 mg/L of a first agent, more preferably, 0.01–0.1 mg/L.

Sickle Cell Anemia

It is believed, without limitation to such theory, that the first agents act to prevent, reduce or ameliorate the restraint on blood flow caused by sickling. Again without limitation to theory, the mode of action is believed to be in reducing vascular as well as blood cell inelasticity. Accordingly, the first agents are used to treat, prevent, reduce or ameliorate a sickle cell anemia.

Erectile Dysfunction

Fibrotic diseases further include diseases that have as a manifestation fibrotic disease of the penis, including Peyronie's disease (fibrosis of the cavernous sheaths leading to contracture of the investing fascia of the corpora, resulting in a deviated and painful erection). Treatment using the invention is expected to treat, prevent, reduce or ameliorate such diseases, or hypertrophy, fibrotic hypertrophy or fibrosis in such diseases.

Without limitation to theory, it is believed that the first agents act to prevent, reduce or ameliorate inelasticity of tissue of the penis and/or fibrosis of tissue of the penis, such as inelasticity or fibrosis of the cavernous sheaths leading to contracture of the investing fascia of the corpora. At least partial restoration of the resulting inelasticity is believed to facilitate engorgement of the corpora cavemosa with blood. Accordingly, the first agents are used to treat, prevent, reduce or ameliorate erectile dysfunction.

Limited Joint Mobility

Limited Joint Mobility (LJM) is a disorder associated with diabetes and typically involves the joints of the hands. The fourth and fifth fingers are affected initially by limitation of motion. AGE glycation and crosslinking of tendons (collagen) in the joints is believed to contribute to the disease. It is believed, without limitation to theory, that the first agents act to prevent, reduce or ameliorate inelasticity, fibrous tissue or cytokine-induced inflammation associated with limited joint mobility. Accordingly, the first agents are used to treat, prevent, reduce or ameliorate limited joint mobility.

Antineoplastic Applications

The first agents inhibit the stimulated formation of bioactive agents, such as VEGF, associated with angiogenesis. Angiogenesis is critical for both normal development and the growth and metastasis of solid tumors. Accordingly, the first agents are used to treat, prevent, reduce or ameliorate the growth of neoplasms by limiting the formation of blood vessels needed to sustain the neoplasms.

End Stage Renal Disease, Diabetic Nephropathy

Diabetic Nephropathy is a complication of diabetes that evolves early, typically before clinical diagnosis of diabetes is made. The earliest clinical evidence of nephropathy is the appearance of low but abnormal levels (>30 mg/day or 20 $\mu$g/min) of albumin in the urine (microalbuminuria), followed by albuminuria (>300 mg/24 h or ~200 $\mu$g/min) that develops over a period of 10–15 years. In patients with type 1 diabetes, diabetic hypertension typically becomes manifest early on, by the time that patients develop microalbuminuria. Once overt nephropathy occurs, the glomerular filtration rate (GFR) falls over several years resulting in End Stage Renal Disease (ESRD) in 50% of type 1 diabetic individuals within 10 years and in >75% of type 1 diabetics by 20 years of onset of overt nephropathy. Albuminuria (i.e., proteinuria) is a marker of greatly increased cardiovascular morbidity and mortality for patients with either type 1 or type 2 diabetes.

Without limitation to theory, it is believed that damage to the glomeruli and blood vessels of the kidney is due to AGE-caused damage, either through protein cross-linking or the stimulation of bioactive agents, or both. Accordingly, the first agents are used to treat, prevent, reduce or ameliorate damage to kidney in patients at risk for ESRD. The first agents can also be used to treat, prevent, reduce or ameliorate glomerulosclerosis.

Hypertension, Isolated Systolic Hypertension

Cardiovascular risk correlates more closely with the systolic and the pulse pressure than with the diastolic pressure. In diabetic patients, the cardiovascular risk profile of diabetic patients is strongly correlated to duration of diabetes, glycemic control and blood pressure. Structural matrix proteins contribute to the function of vessels and the heart, and changes in the physical behavior of cardiovascular walls are believed to be important determinants of circulatory function. In elderly individuals, the loss of compliance in the aorta leads to isolated systolic hypertension, which in turn expands the arterial wall and thereby diminishes the dynamic range of elasticity. Loss of compliance also results in the development of left ventricular hypertrophy. In vivo studies in rodents, canines and in primates indicate potential utility of 3-[2-phenyl-2-oxoethyl]-4,5-dimethyl-thiazolium salt in substantially ameliorating vascular stiffening. For example, in a dog model for diabetes, lower end diastolic pressure and increased end diastolic volume, indicators of ventricular elasticity, returned to a value at about the midpoint between the disease impaired value and the value for control dogs. Treatment with 3-[2-phenyl-2-oxoethyl]-4,5-dimethyl-thiazolium salt lead to a reduction in the mass of collagen in cardiovascular tissues. In situ hybridization studies demonstrate that 3-[2-phenyl-2-oxoethyl]-4,5-dimethyl-thiazolium salt reduces the expression of both Type IV collagen and TGFbeta.

Compared with that of a non-diabetic, the diabetic artery is smaller as it is stiffer. As in isolated systolic hypertension in which vessels stiffen with age and lose the dynamic range of expansion under systole. First agents are used to treat, prevent, reduce or ameliorate hypertension, including isolated systolic hypertension and diabetic hypertension. Moreover, the same benefit is anticipated for the more rare hypertensive disorder, pulmonary hypertension. Pulmonary hypertension is a rare blood vessel disorder of the lung in which the pressure in the pulmonary artery (the blood vessel that leads from the heart to the lungs) rises above normal levels and may become life threatening. The similarity in development of elevated blood pressure in the pulmonary bed with the increase in systemic blood pressure in diabetic hypertension and in isolated systolic hypertension suggests similar mechanisms are involved.

Pulse pressure is the difference between systolic and diastolic blood pressure. In a young human, systolic pressure is typically 120 mm Hg and diastolic pressure is 80 mm Hg, resulting in a pulse pressure of 40 mm Hg. With age, in many individuals pulse pressure increases, largely due to the increase in systolic pressure that results from stiff vessel disease. In individuals with pulse pressure greater than 60 mm Hg there is an increased risk of death from cardiovascular morbidities. In a Phase IIa trial, one compound believed to work by a mechanism shared by the compounds of the invention, 3-[2-phenyl-2-oxoethyl]-4,5-dimethyl-thiazolium salt, reduced pulse pressure in elderly patients with pulse pressures greater than 60 mm Hg in a statistically significant manner. This decrease in pulse pressure was believed to be due primarily to the effect of the agent on lowering the systolic blood pressure.

The agents of the invention are used to treat, prevent, reduce or ameliorate reduced vascular compliance, elevated pulse pressure, hypertension and left ventricular hypertrophy. Moreover, the agents are used to reduce pulse pressure, increase vascular compliance, or decrease the risk of death.

Heart Failure

Congestive Heart Failure (CHF) is a clinical syndrome that entails cardiac disease of the ventricle. Diastolic dysfunction is a subset of heart failure in which the left ventricle stiffens with age. The stiffening of the left ventricle that occurs in CHF and in diastolic dysfunction is believed to result from increased crosslinking of collagen fibers with age and/or fibrosis and related hypertrophy. First agents are used to treat, prevent, reduce or ameliorate heart failure.

Retinopathy

The effect of diabetes on the eye is called diabetic retinopathy and involves changes to the circulatory system of the retina. The earliest phase of the disease is known as background diabetic retinopathy wherein the arteries in the retina become weakened and leak, forming small, dot-like hemorrhages. These leaking vessels often lead to swelling or edema in the retina and decreased vision. The next stage is proliferative diabetic retinopathy, in which circulation problems cause areas of the retina to become oxygen-deprived or ischemic. New vessels develop as the circulatory system attempts to maintain adequate oxygen levels within the retina. Unfortunately, these new vessels hemorrhage easily. In the later phases of the disease, continued abnormal vessel growth and scar tissue may cause serious problems such as retinal detachment. First agents are used to treat, prevent, reduce or ameliorate diabetic retinopathy. The fisrt agents can be administered by the methods described below, including by topical administration to the eye. The agents can also be administered by intravitreal implant.

Cataracts, Other Damage to Lens Proteins

AGE-mediated crosslinking and/or fibrotic processes are believed to contribute to cataract formation and formation of other damage to lens proteins. First agents are used to treat, prevent, reduce or ameliorate cataracts or other damage to lens proteins.

Atzheimer's Disease

Considerable evidence exists implicating AGEs that form in the neurofibrillary tangles (tau protein) and senile plaques (beta-amyloid peptide) in early neurotoxic processes of Alzheimer's disease. Insoluble human tau protein is likely crosslinked. Glycation of insoluble tau from AD patients and experimentally AGE-modified tau generate oxygen free radicals, resulting in the activation of transcription via nuclear factor-kappa B, and resulting in an increase in amyloid beta-protein precursor and release of amyloid beta-peptides. Thus, A.G.E.-modified tau may function as an initiator in a positive feedback loop involving oxidative stress and cytokine gene expression. First agents are used to treat, prevent, reduce or ameliorate Alzheimer's disease.

Other Indications

For reasons analogous to those set forth above, the invention is believed to be useful in treating, preventing, reducing or ameliorating diabetes or its associated adverse sequelae, and peripheral neuropathy. The agents, especially in topical form, increase elasticity and/or reduce wrinkles in skin. The agents further increase red blood cell deformability.

Combination Therapies

In cardiovascular therapies, first agents can be administered concurrently or in a combined formulation with one or more antioxidants. Examples of appropriate antioxidants are vitamin A, vitamin B6, vitamin C, vitamin E, glutathione, β-carotene, α-lipoic acid, coenzyme Q10, selenium and zinc, which are administered in effective amounts as is known in the art. Thus, the invention further provides pharmaceutical compositions comprising an agent of the invention in combination with an effective amount of an antioxidant.

In treating heart failure, cardiomyopathy or heart attack, first agents can be administered concurrently or in a combined formulation with one or more angiotensin converting enzyme (ACE) inhibitors, angiotensin II receptor antagonists, calcuim channel blockers, diuretics, digitalis or beta blockers. Examples of ACE inhibitors include Captopril, Enalapril, Enalaprilat, Quinapril, Lisinopril and Ramipril, which are administered in effective amounts as is known in the art. Examples of angiotensin II receptor antagonists include Losartan, Irbesartan, Eprosartan, Valsartan and Candesartan, which are administered in effective amounts as is known in the art. Examples of calcium channel blockers include Amlopdipine, Bepridil, Diltiazem, Felodipine, Isradipine, Nicardipine, Nifedipine, Nimodipine and Verapamil, which are administered in effective amounts as is known in the art. Among diuretics, preferred examples include Furosemide, Bumetanide, Torsemide, Ethacrynic acid, Azosemide, Muzolimine, Piretanide, Tripamide and Hydrochlorothiazide, which are administered in effective amounts as is known in the art. Examples of beta adrenergic antagonists include Metoprolol, Carvedilol, Bucindolol, Atenolol, Esmolol, Acebutolol, Propranolol, Nadolol, Timolol, Pindolol, Labetalol, Bopindolol, Carteolol, Penbutolol, Medroxalol, Levobunolol, Bisoprolol, Nebivolol, Celiprolol and Sotalol, which are administered in effective amounts as is known in the art. Thus, the invention further provides pharmaceutical compositions comprising an agent of the invention in combination with an effective amount of an ACE inhibitor, diuretic, digitalis, beta blocker, or combination thereof.

For treating diabetes or complications thereof, the invention further provides pharmaceutical compositions comprising an agent of the invention in combination with an effective amount of a thiazolidinedione or "glitazone" diabetes drug, such as Troglitazone, Rosiglitazone, and Pioglitazone.

In treating atherosclerosis, first agents can be administered concurrently or in a combined formulation with one or more statins (HMG CoA reductase inhibitors) or cholestyramine. Examples of statins include Mevastatin, Lovastatin, Simvastatin, Pravastatin and Fluvastatin, which are administered in effective amounts as is known in the art. Thus, the invention further provides pharmaceutical compositions comprising an agent of the invention in combination with an effective amount of a statin, cholestyramine, or both.

For a number of indications discussed, including sickle cell anemia and diabetic complications, as well as wound healing and any other indication in which increased tissue perfusion is a useful means or adjunct to therapy, the first agents, or aminoguanidine or other agents of the aminoguanidine class can be administered with erythropoietin, which is administered in effective amount as is known in the art. Erythropoietin includes stable forms of erythropoietin such as are marketed by Amgen (Thousand Oaks, Calif.).

For all indications, agents can be administered concurrently or in a combined formulation with aminoguanidine or other agents of the aminoguanidine class, which are administered in effective amounts as is known in the art. These agents include compounds of formula A

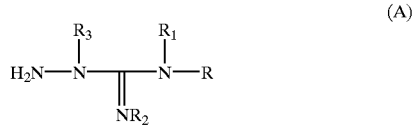

(A)

wherein R is an alkyl group, or a group of the formula —N($R^4$)($R^5$) wherein $R^4$ is hydrogen, and $R^5$ is an alkyl group or a hydroxyalkyl group; or $R^4$ and $R^5$ together with the nitrogen atom are a heterocyclic group containing 4–6 carbon atoms and, in addition to the nitrogen atom, 0–1 oxygen, nitrogen or sulfur atoms; $R^1$ is hydrogen or an amino group; $R^2$ is hydrogen or an amino group; $R^3$ is hydrogen or an alkyl group, wherein R and $R^1$ cannot both be amino groups. Preferably at least one of $R^1$, $R^2$, and $R^3$ is other than hydrogen. The compounds can be used as their pharmaceutically acceptable acid addition salts, and mixtures of such compounds. When aminoguanidine compounds are administered, they can be administered by any route of pharmaceutical administration including those discussed below for other first agents.

The method of the invention is used to treat animals, preferably mammals, preferably humans.

In accordance with the present invention, methods for administering pharmaceutical compositions containing compounds have been developed for the treating the indications of the invention. These agents are derived from heteroaromatic 5-membered or fused bicyclic rings, as shown in Scheme 1 below:

Scheme 1

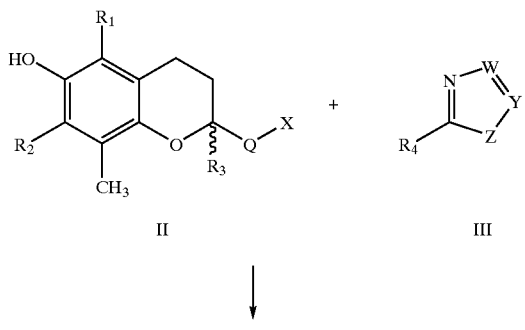

II  III

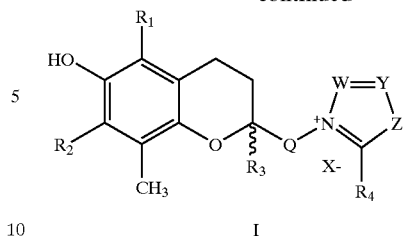

I

Preferred compounds of the present invention include compounds derived from the heterocycles defined by III, including, but not limited to, oxazoles, thiazoles, imidazoles, [1,3,4]- and [1,2,4]-oxadiazoles, [1,3,4]- and [1,2,4]-thiadiazoles, [1,2,4]-triazoles, benzoxazoles, and benzothiazoles and the like, by their treatment with the 6-chromane derivative II, neat, or in a suitable polar solvent, such as acetonitrile, dimethylformamide, N-methyl-pyrrolidone, dimethylsulfoxide, methanol or ethanol, or aqueous mixtures of these organic solvents, at from room temperature to 60° C. for from 1 to 96 hours. (See Scheme 1.)

It is recognized by those skilled in the art that pyrazoles, indazoles, benzothiazoles, benzoisothiazoles, isothiazoles, isoxazoles, benzisoxazoles, [1,2,3]-triazoles, [1,2,3]-oxadiazoles and [1,2,3]-thiadiazoles may be treated with II to prepare analogous azolium salts, which are not explicitly described by structure I in Scheme 1.

It is further recognized by those skilled in the art that when either W or Y=N (Scheme 1, structure III), alkylation of III may also occur on that nitrogen, in addition to the alkylation on the nitrogen atom shown in product I, to yield mixtures of product. In this situation, the addition of one equivalent or less of a suitable acid, such as the appropriate volume of an ethereal HCl or ethereal HBr solution prior to the addition of III, will alter the ratio of the isomers formed. Where isomeric addition products are formed, they may be separated by chromatographic methods such as HPLC or, more preferably, by selective crystallization.

It will also be recognized by those skilled in the art that the carbon of the chromane structure bearing the group Q is asymmetric and can exist in one of two configurations, (R) or (S). When equal mixtures of (R) and (S) forms are present, the compound exists as a non-optically active racemic mixture. The present invention covers the racemates and each single, optically pure or enriched enantiomeric derivative. It will further be recognized that the tools for isolating enantiomers with chiral specific chromatographic methods and crystallographic methods (typically using chiral salts) have developed to make such isolations generally applicable.

The alkyl, and alkenyl groups referred to below include both $C_1$ to $C_6$ linear and branched alkyl and alkenyl groups, unless otherwise noted. In addition, alkoxy groups include linear or branched $C_1$ to $C_6$ alkoxy groups, unless otherwise noted. Alkyl' represents a second alkyl group independently selected from the same $C_1$ to $C_6$ linear or branched selection.

Consistent with the rules of aromaticity, Ar, or aryl, refers to a $C_6$ or $C_{10}$ aromatic ring, optionally substituted as set forth below, or a 5- or 6-membered heteroaromatic (heteroaryl) ring containing at least one and up to three atoms of N for the 6-membered heteroaryl ring and from one to three atoms of N or one atom of O or S and zero to two atoms of N for the 5-membered heteroaryl ring; each heteroaromatic ring can be substituted with up to two amino-, dialkylamino-, pyrrolidin-1-yl, piperidin-1-yl, morpholin-4-yl, thiamorpholin-4-yl, 4-(aryl)piperidin-1-yl, 4-(aryl)

piperazin-1-yl- (said aryl group optionally substituted as described below), halo (particularly fluoro) or alkylenedioxy groups, or fused to a substituted benzene, pyridine, pyrimidine, pyridazine or triazine ring, and wherein $C_6$ or $C_{10}$ aromatic and heteroaromatic rings can be additionally substituted as set forth below.

$C_6$ or $C_{10}$ aromatic rings can be additionally substituted with acylamino, acyloxyalkyl, alkanoyl, alkanoylalkyl, alkenyl, alkoxy, alkoxycarbonyl, alkoxycarbonylalkyl, alkyl, alkylamino, $(C_1–C_3)$-alkylenedioxy, alkylsulfonyl, alkylthio, allyl, amino, benzoyl, carboxy, carboxyalkyl, cyano, cycloalkyl, dialkylamino, halo, fluoromethyl, difluoromethyl, trifluoromethyl, hydroxy, $(C_1–C_6)$-hydroxyalkyl, mercapto, nitro, phenoxy, phenyl, phenylalkyl, sulfamoyl, sulfo (—$SO_3H$), aminosulfonyl ($H_2NSO_2$—), phenylsulfonyl, or phenylsulfinyl.

Heteroaromatic rings can be additionally substituted with acylamino, alkanoyl, alkoxy, alkoxycarbonyl, Other related salts can be formed using similarly non-toxic, and biologically and pharmaceutically acceptable anions.

Compounds of the formula II can be conveniently prepared by chemical methods well known in the art. The known acid IV (trolox; see Scheme 2), or its phenol protected derivatives IVa, IVb and IVc may be treated with lithium hydride at 0° C. in a dry, ethereal solvent for one hour, followed by treatment with methyl lithium in ether at the same temperature. The deprotected methyl ketone isolated after acidification and purification may then be treated with bromine to generate II (X=Br). Alternatively, IV may be treated with thionyl chloride, the acid chloride isolated and treated with diazomethane followed by HCl and deprotection to afford the corresponding chloroketone, II (X=Cl).

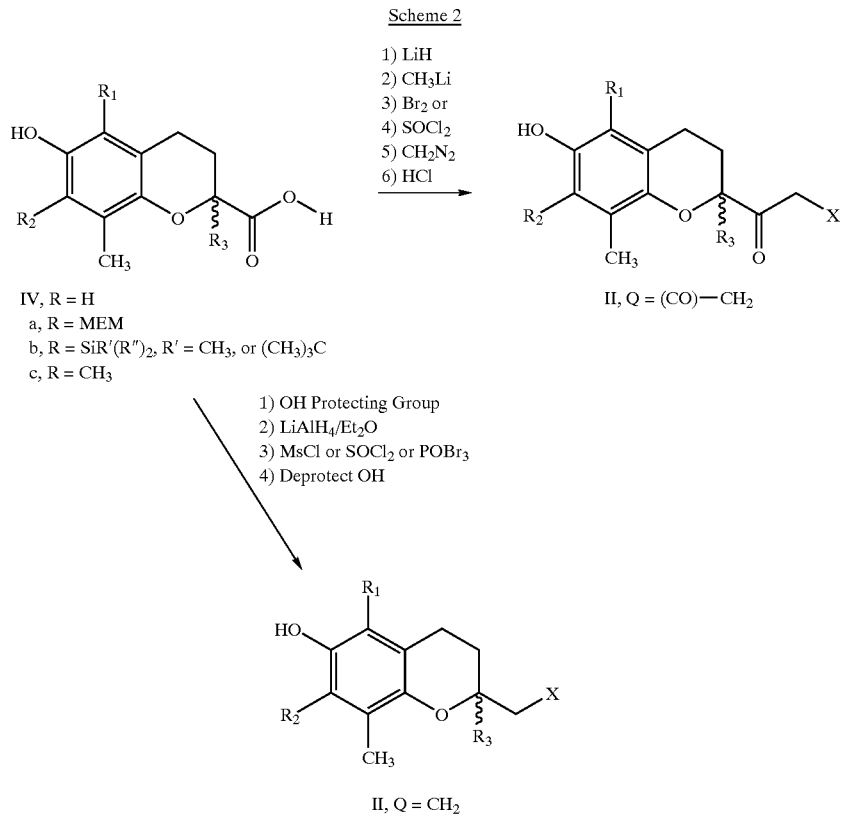

alkoxycarbonylalkyl, alkyl, alkylamino, alkylsulfonyl, alkylthio, amino, arylsulfonyl, aryl sulfonyl, benzoyl, carboxy, cyano, dialkylamino, halo, fluoralkyl, hydroxy, mercapto, nitro, phenyl, phenoxy, pyrrolidin-1-yl, piperidin-1-yl, 4-arylpiperidin-1-yl, morpholin-4-yl, 4-arylpiperazin-1-yl, sulfamoyl, fluoromethyl, difluoromethyl, or trifluoromethyl.

The halo atoms can be fluoro, chloro, bromo or iodo. X⁻ is a pharmaceutically acceptable anion.

The compounds of formula I comprise biologically and pharmaceutically acceptable salts. Useful salt forms include the halides, particularly bromide and chloride, brosylate, tosylate, methanesulfonate (mesylate), and mesitylenesulfonate salts. It is recognized that appropriate acetate, fumarate, maleate and succinate derivatives may be prepared from the chloride salt via ion exchange techniques.

As is recognized many of the nitrogen containing heterocycles of the invention (compounds of formula III) are commercially available from chemical supply houses or are readily synthesized by methods well known in the art. For instance, certain substitution patterns can be obtained by electrophilic and nucleophilic substitution reactions on the heterocycle and are well known in the art. In addition selected nitrogen heterocycles are susceptible to metalation with organoalkali reagents, for example, n-butyllithium. The intermediate metalated-heterocycles can be treated with electrophiles, such as methyl iodide, formaldehyde, acetaldehyde, acetone, methyl pyruvate and others, to provide additional routes to specifically substituted aromatic nitrogen heterocycles.

Certain aromatic nitrogen containing heterocycles can be obtained by cyclization and cycloaddition reactions of substituted acyclic precursors that are well known in the art. Non-limiting examples of such syntheses are described below.

The pyrazole compounds of the invention can be prepared by reaction of hydrazine derivatives with 1,3-dicarbonyl compound (Scheme 3). For example, 1,3-diketones having aryl substituents can be used to prepare 3-arylpyrazole (i.e. Y=Ar) compounds. As will be recognized by those in the art, use of unsymmetrically substituted 1,3-dicarbonyl compounds with alkyl or aryl hydrazines often lead to isomeric mixtures of pyrazole products. These isomeric mixtures can be separated by well-known separation techniques such as fractional crystallization, column chromatography, and the like.

Scheme 3

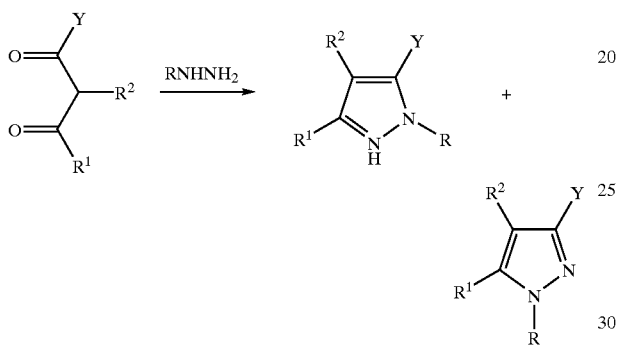

3-Aminopyrazole compounds (Y=NH$_2$) of the invention can be prepared by reaction of aryl hydrazones with ketones and aldehyde containing an a-nitrile moiety (Scheme 4, Bouveault, M. L. *Bull. Soc. Chim. Fr.,* 1890, 4, 647). 3-Aminopyrazoles can also serve as intermediates for 3-acylamino-, 3-ureido-, and 3-thioureidopyrazoles of the invention. For example, 3-aminopyrazoles can be heated with esters to form 3-acylaminopyrazoles of the invention. The 3-aminopyrazoles are heated with formic acid to provide 3-formylaminopyrazoles. Likewise, treatment of 3-aminopyrazoles with isocyanates and isothiocyanates lead to the 3-ureido and 3-thioureido compounds (respectively) of the invention.

Indazoles of the invention substituted with alkyl and aryl substituents at the 3-position are synthesized from benzene analogs containing ortho-halo ketones and aldehydes (Scheme 5). For example, an indazole containing a 3-phenyl substituent can be prepared from a benzophenone analog containing a bromo moiety ortho to the carbonyl.

Scheme 5

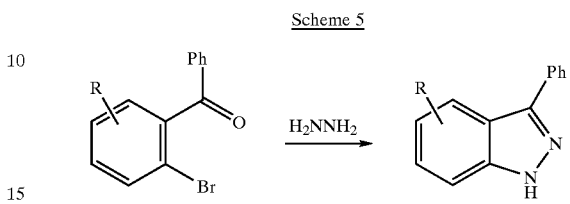

3-aminoindazoles are similarly prepared from substituted benzene precursors. A 2-azidobenzonitrile can be treated with hydrazine to prepared 3-aminoindazoles of the invention (Scheme 6, Paterson, T. M.; Smalley, R. K.; Sushizky *Tetrahedron Lett.,* 1977, 3973). 3-Acylamino-, 3-ureido-, and 3-thioureidoindazoles of the invention can be prepared from the 3-aminoindazoles using esters, isocyanates, and isothiocyanates (as described above using 3-aminopyrazoles).

Scheme 6

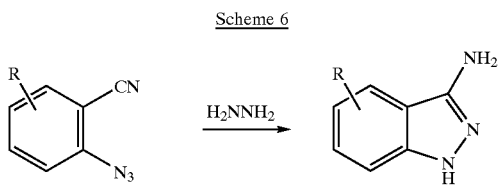

3- and 5-Aryl and alkyl isoxazoles of the invention are prepared by use of the chloro substituted α,β-unsaturated ketones with hydroxylamine (Scheme 7). The isomeric products can be isolated by separation techniques such as fractional crystallization, distillation, or column chromatography. Alternatively, 5-aryl substituted isoxazoles can be prepared from acetophenones (Scheme 7, Lin, Y. Lang, S. A. *J. Heterocyclic Chem.,* 1977, 14, 355).

Scheme 4

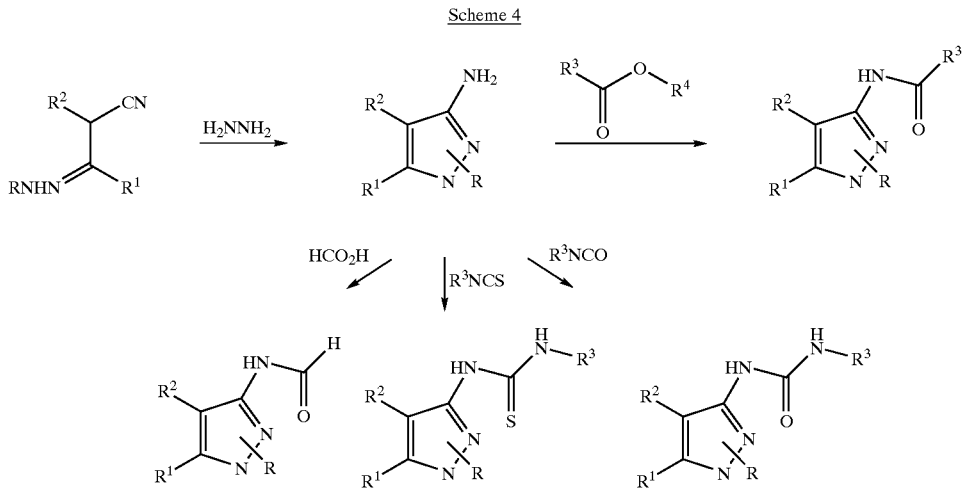

Scheme 7

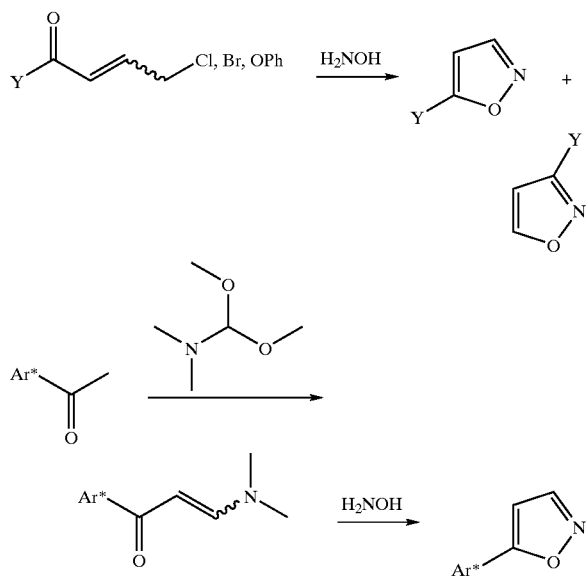

5-Aminoisoxazoles of the invention can be prepared from α-halo substituted oximes by reaction with sodium cyanide (Scheme 8, Lozanovic, M. et al. *Chem. Abstr.*, 1981, 94, 192202c). The 5-amino group can be reacted with the reagents described above for 3-aminopyrazoles to provide acylamino-, ureido-, and thioureido isoxazoles of the invention.

Scheme 8

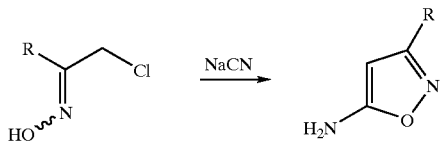

Alkyl and aryl substituted isothiazoles of the invention are prepared by the cyclization of β-imino thionocarbonyl compounds (Scheme 9). Oxidizing reagents well known in the art such as peroxides, chloranil, iodine, and the like, promote the cyclization. For example, starting material with an aryl thionocarbonyl group β-substituted to an imino group can be used to prepare a 5-aryl substituted isothiazole.

Scheme 9

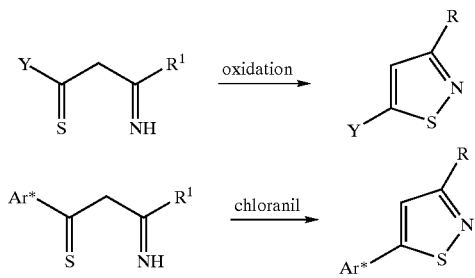

5-Amino isothiazoles of the invention can be prepared similarly (Scheme 10). Enamines can be treated with isothiocyanates to yield thioamide intermediates. The thioamides can be cyclized using oxidizing agents to provide 5-aminoisothiazoles of the invention. The 5-amino group can be reacted with the reagents described above for the 3-aminopyrazoles to provide acylamino-, formylamino-, ureido-, and thioureido-isoxazoles of the invention.

Scheme 10

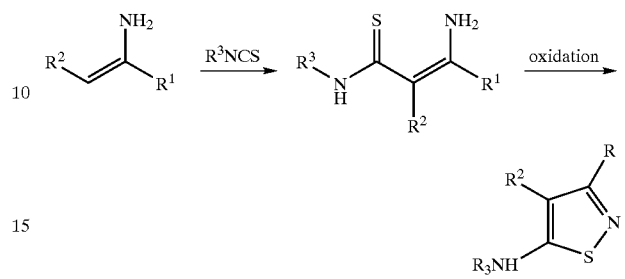

Aryl and alkyl 1,2,4-triazoles of the invention are prepared from acyl amidrazones as shown in Scheme 11. Amino-substituted 1,2,4-triazoles are formed analogously from acylaminoguanidine precursors.

Scheme 11

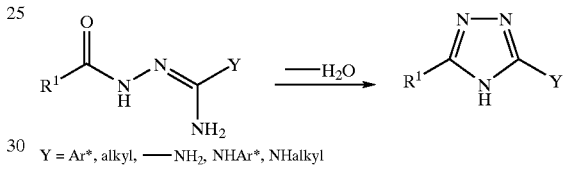

Y = Ar*, alkyl, ——NH$_2$, NHAr*, NHalkyl

To treat the indications of the invention, an effective amount of a pharmaceutical compound will be recognized by clinicians but includes an amount of a compound of the formula I effective to treat, reduce, ameliorate, eliminate or prevent one or more symptoms of the disease sought to be treated or the condition sought to be avoided or treated, or to otherwise produce a clinically recognizable change in the pathology of the disease or condition.

Pharmaceutical compositions can be prepared to allow a therapeutically effective quantity of the compound of the present invention, and can include a pharmaceutically acceptable carrier, selected from known materials utilized for this purpose. See, e.g., Remington, The Science and Practice of Pharmacy, 1995; Handbook of Pharmaceutical Excipients, 3$^{rd}$ Edition, 1999. Such compositions can be prepared in a variety of forms, depending on the method of administration.

In addition to the subject compound, the compositions of this invention can contain a pharmaceutically-acceptable carrier. The term "pharmaceutically-acceptable carrier", as used herein, means one or more compatible solid or liquid filler diluents or encapsulating substances that are suitable for administration to an animal, including a mammal or human. The term "compatible", as used herein, means that the components of the composition are capable of being commingled with the subject compound, and with each other, such that there is no interaction that would substantially reduce the pharmaceutical efficacy of the composition under ordinary use. Preferably when liquid dose forms are used, the compounds of the invention are soluble in the components of the composition. Pharmaceutically-acceptable carriers must, of course, be of sufficiently high purity and sufficiently low toxicity to render them suitable for administration to the animal being treated.

Some examples of substances which can serve as pharmaceutically-acceptable carriers or components thereof are sugars, such as lactose, glucose and sucrose; starches, such as corn starch and-potato starch; cellulose and its derivatives, such as sodium carboxyrnethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the subject compound is basically determined by the way the compound is to be administered. If the subject compound is to be injected, the preferred pharmaceutically-acceptable carrier is sterile, physiological saline, with a blood-compatible suspending agent, the pH of which has been adjusted to about 7.4.

If the preferred mode of administering the subject compound is perorally, the preferred unit dosage form is therefore tablets, capsules, lozenges, chewable tablets, and the like. Such unit dosage forms comprise a safe and effective amount of the subject compound, which is preferably from about 0.7 or 3.5 mg to about 280 mg/70 kg, more preferably from about 0.5 or 10 mg to about 210 mg/70 kg. The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder-mixture. Coloring agents, such as the FD & C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of this invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.012% to about 0.933% of the subject compound, more preferably from about 0.033% to about 0.7%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Compositions can also be used to deliver the compound to the site where activity is desired; such as eye drops, gels and creams for ocular disorders.

Compositions of this invention include solutions or emulsions, preferably aqueous solutions or emulsions comprising a safe and effective amount of a subject compound intended for topical intranasal administration. Such compositions preferably comprise from about 0.01% to about 10.0% w/v of a subject compound, more preferably from about 0.1% to about 2.0%. Similar compositions are preferred for systemic delivery of subject compounds by the intranasal route. Compositions intended to deliver the compound systemically by intranasal dosing preferably comprise similar amounts of a subject compound as are determined to be safe and effective by peroral or parenteral administration. Such compositions used for intranasal dosing also typically include safe and effective amounts of preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acids and bases to adjust the pH of these aqueous compositions as needed. The compositions may also comprise local anesthetics or other actives. These compositions can be used as sprays, mists, drops, and the like.

Other preferred compositions of this invention include aqueous solutions, suspensions, and dry powders comprising a safe and effective amount of a subject compound intended for atomization and inhalation administration. Such compositions are typically contained in a container with attached atomizing means. Such compositions also typically include propellants such as chlorofluorocarbons 12/11 and 12/114, and more environmentally friendly fluorocarbons, or other nontoxic volatiles; solvents such as water, glycerol and ethanol, these include cosolvents as needed to solvate or suspend the active; stabilizers such as ascorbic acid, sodium metabisulfite; preservatives such as cetylpyidinium chloride and benzalkonium chloride; tonicity adjustors such as sodium chloride; buffers; and flavoring agents such as sodium saccharin. Such compositions are useful for treating respiratory disorders, such as asthma and the like.

Other preferred compositions of this invention include aqueous solutions comprising a safe and effective amount of a subject compound intended for topical intraocular administration. Such compositions preferably comprise from about 0.01% to about 0.8% w/v of a subject compound, more preferably from about 0.05% to about 0.3%. Such compositions also typically include one or more of preservatives, such as benzalkonium chloride or thimerosal, vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases can be used to adjust the pH of these formulations as needed.

Other preferred compositions of this invention useful for peroral administration include solids, such as tablets and capsules, and liquids, such as solutions, suspensions and emulsions (preferably in soft gelatin capsules), comprising a safe and effective amount of a subject compound. Such compositions can be coated by conventional methods, typically with pH or time-dependent coatings, such that the subject compound is released in the gastrointestinal tract at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit™ coatings, waxes and shellac.

The compounds of the invention are administered by ocular, oral, parenteral, including, for example, using formulations suitable as eye drops. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. See, Remington's Pharmaceutical Sciences, 16th Ed., Mack Publishing, Easton, Pa., 1980, as well as later editions, for information on pharmaceutical compounding.

Numerous additional administration vehicles will be apparent to those of ordinary skill in the art, including without limitation slow release formulations, liposomal formulations and polymeric matrices.

In another preferred embodiment, the pharmaceutically effective amount is approximately 0.1 or 0.5 to 4 mg/kg body weight daily. Still more preferably, the pharmaceutically effective amount is approximately 1 mg/kg body weight daily. In a preferred embodiment, the amount is administered in once daily doses, each dose being approximately 1 mg/kg body weight.

The activity of the compounds of the invention in breaking, reversing or inhibiting the formation of AGE's or AGE-mediated crosslinks can be assayed by any of the methods described in U.S. Pat. No. 5,853,703.

Except where heteroaryl is separately recited for the same substituent, the term "heterocycle" includes heteroaryl.

Where noted above, publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

arylWhat is claimed:

1. A method of treating, reducing or ameliorating reduced vascular compliance, elevated pulse pressure, hypertension or left ventricular hypertrophy in a subject in need thereof comprising administering an effective amount of a compound of the formula I:

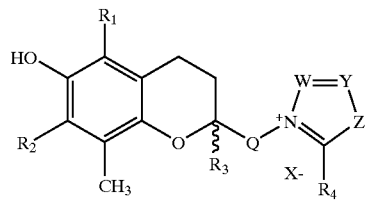

wherein:

W and Y are independently N, $CR^W$ or $CR^Y$;

Z is O, S or $NR^Z$;

Q is —$CH_2$— or —(CO)—$CH_2$—, where the methylene is bonded to a ring nitrogen;

$R^W$ and $R^Y$ are independently hydrogen, alkyl, —C≡$CR^E$, —$CH_2$—C≡$CR^P$, alkenyl, aryl, arylalkyl, aryloxy, arylthio, amino, alkylamino, arylamino, dialkylamino, diarylamino, $CH_3C(O)NH$—, fluoroalkyl, perfluoroaryl, hydroxyalkyl, $C(O)NH_2$, or $S(O)_2NH_2$ or, together with their ring carbon atoms form a fused 6-membered aromatic or heteroaromatic ring, wherein $R^E$ or $R^P$ is alkyl, hydrogen, hydroxyalkyl or aryl;

$R^Z$ is alkyl, —$CH_2$—C≡$CR^P$, aryl, arylalkyl, or aroylalkyl;

$R^1$ and $R^2$ are independently hydrogen, alkyl or hydroxymethyl;

$R^3$ is hydrogen or methyl;

$R^4$ is acetamido, hydrogen, methyl, amino, —C≡$CR^E$, —$CH_2$—C≡$CR^P$, alkylthio, fluoromethyl, difluoromethyl, trifluoromethyl, cyanomethyl, hydroxyalkyl, alkoxycarbonyl-methyl, 1-(alkoxycarbonyl)-1-hydroxyalkyl or aminocarbonyl-methyl;

aryl is a $C_6$ or $C_{10}$ aromatic ring, optionally substituted as set forth below, or a 5- or 6-membered heteroaromatic (heteroaryl) ring containing at least one and up to three atoms of N for the 6-membered heteroaryl ring and from one to three atoms of N or one atom of O or S and zero to two atoms of N for the 5-membered heteroaryl ring; each heteroaromatic ring can be substituted with up to two amino-, dialkylamino-, pyrrolidin-1-yl, piperidin-1-yl, morpholin-4-yl, thiamorpholin-4-yl, 4-(aryl)piperidin-1-yl, 4-(aryl)piperazin-1-yl- (said aryl group being $C_6$ or $C_{10}$ and optionally substituted as described below), halo or alkylenedioxy groups, or fused to a substituted benzene, pyridine, pyrimidine, pyridazine or triazine ring, and wherein said heteroaromatic rings can be additionally substituted;

said $C_6$ or $C_{10}$ aromatic rings can be additionally substituted with acylamino, acyloxyalkyl, alkanoyl, alkanoylalkyl, alkenyl, alkoxy, alkoxycarbonyl, alkoxycarbonylalkyl, alkyl, alkylamino, ($C_1$–$C_3$)-alkylenedioxy, alkylsulfonyl, alkylthio, allyl, amino, benzoyl, carboxy, carboxyalkyl, cyano, cycloalkyl, dialkylamino, halo, fluoromethyl, difluoromethyl, trifluoromethyl, hydroxy, ($C_1$–$C_6$)-hydroxyalkyl, mercapto, nitro, phenoxy, phenyl, phenylalkyl, sulfamoyl, sulfo (—$SO_3H$), aminosulfonyl ($H_2NSO_2$—), phenylsulfonyl, or phenylsulfinyl;

said heteroaromatic rings can be additionally substituted with acylamino, alkanoyl, alkoxy, alkoxycarbonyl, alkoxycarbonylalkyl, alkyl, alkylamino, alkylsulfonyl, alkylthio, amino, arylsulfonyl, aryl sulfonyl, benzoyl, carboxy, cyano, dialkylamino, halo, fluoroalkyl, hydroxy, mercapto, nitro, phenyl, phenoxy, pyrrolidin-1-yl, piperidin-1-yl, 4-arylpiperidin-1-yl, morpholin-4-yl, 4-arylpiperazin-1-yl, sulfamoyl, fluoromethyl, difluoromethyl, or trifluoromethyl;

the halo atoms are fluoro, chloro, bromo or iodo; and

X⁻ is a pharmaceutically acceptable anion;

or pharmaceutically acceptable acid addition salts of said compounds to said subject.

2. The method of claim 1, wherein anion X— is chloride, bromide, mesylate, tosylate, brosylate, mesitylene sulfonate, fumarate, maleate or acetate.

3. The method of claim 1 comprising administering an effective amount of a compound of the formula I, wherein:

$R^W$ and $R^Y$ are independently hydrogen, alkyl, aryloxy, arylthio, amino, alkylamino, dialkylamino, $CH_3C(O)NH$—, fluoroalkyl, perfluoroaryl, or hydroxyalkyl or, together with their ring carbon atoms form a fused 6-membered aromatic or heteroaromatic ring;

R1 and R2 are methyl;

aryl is a $C_6$ or $C_{10}$ aromatic ring, optionally substituted as set forth below, or a 5- or 6-membered heteroaromatic (heteroaryl) ring containing at least one and up to three atoms of N for the 6-membered heteroaryl ring and from one to three atoms of N or one atom of O or S and zero to two atoms of N for the 5-membered heteroaryl ring; each heteroaromatic ring can be substituted with up to two amino-, dialkylamino-, pyrrolidin-1-yl, piperidin-1-yl, morpholin-4-yl, thiamorpholin-4-yl, 4-(aryl)piperidin-1-yl, 4-(aryl)piperazin-1-yl- (said aryl group being $C_6$ or $C_{10}$ and optionally substituted as described below), halo or fused to a substituted benzene ring, and wherein said heteroaromatic rings can be additionally substituted;

said $C_6$ or $C_{10}$ aromatic rings can be additionally substituted with acylamino, acyloxyalkyl, alkanoyl, alkanoylalkyl, alkenyl, alkoxy, alkoxycarbonyl, alkoxycarbonylalkyl, alkyl, alkylamino, $(C_1-C_3)$-alkylenedioxy, alkylsulfonyl, alkylthio, allyl, amino, benzoyl, carboxy, carboxyalkyl, cycloalkyl, dialkylamino, halo, fluoromethyl, difluoromethyl, trifluoromethyl, hydroxy, $(C_2-C_6)$-hydroxyalkyl, mercapto, nitro, phenoxy, phenyl, phenylalkyl, sulfamoyl, sulfo, aminosulfonyl, phenylsulfonyl, or phenylsulfinyl;

said heteroaromatic rings can be additionally substituted with acylamino, alkanoyl, alkoxy, alkoxycarbonyl, alkoxycarbonylalkyl, alkyl, alkylamino, alkylsulfonyl, alkylthio, amino, arylsulfonyl, aryl sulfonyl, benzoyl, carboxy, dialkylamino, halo, fluoralkyl, hydroxy, mercapto, nitro, phenyl, phenoxy, pyrrolidin-1-yl, piperidin-1-yl, 4-arylpiperidin-1-yl, morpholin-4-yl, 4-arylpiperazin-1-yl, sulfamoyl, fluoromethyl, difluoromethyl or trifluoromethyl; and the halo atoms are fluoro, chloro or bromo.

4. The method of claim 3 comprising administering an effective amount of a compound of the formula I, wherein:

W and Y are $CR^W$ and $CR^Y$, respectively;

Z is S, and the compounds are thiazolium salts; and $R^4$ is acetamido, hydrogen, methyl, amino, alkylthio, fluoromethyl, difluoromethyl or trifluoromethyl.

5. The method of claim 3 comprising administering an effective amount of a compound of the formula I, wherein:

W is N and Y is $CR^Y$;

Z is S, and the compounds are [1,3,4]-thiadiazolium salts;

$R^Y$ is hydrogen, alkyl, aryloxy, arylthio, amino, alkylamino, dialkylamino, fluoroalkyl, perfluoroaryl, or hydroxyalkyl; and $R^4$ is acetamido, hydrogen, methyl, amino, alkylthio, fluoromethyl, difluoromethyl or trifluoromethyl.

6. The method of claim 3 comprising administering an effective amount of a compound of the formula I, wherein:

$R^4$ is hydrogen, methyl, amino, alkylthio, fluoromethyl or difluoromethyl.

7. The method of claim 6 comprising administering an effective amount of a compound of the formula I, wherein $Q=$—(CO)—$CH_2$—.

8. The method of claim 7 comprising administering an effective amount of a compound of the formula I, wherein:

W is N and Y is $CR^Y$; and

Z is O and the compounds are [1,3,4]-oxadiazolium salts; and $R^Y$ is hydrogen, alkyl, aryloxy, arylthio, amino, alkylamino, dialkylamino, fluoroalkyl, perfluoroaryl, or hydroxyalkyl.

9. The method of claim 7 comprising administering an effective amount of a compound of the formula I, wherein:

W is N and Y is $CR^Y$;

Z is $NR^Z$ and the compounds are [1,2,4]-triazolium salts; and $R^Y$ is hydrogen, alkyl, aryloxy, arylthio, amino, alkylamino, dialkylamino, fluoroalkyl, perfluoroaryl, or hydroxyalkyl.

10. The method of claim 7 comprising administering an effective amount of a compound of the formula I, wherein:

W and Y are $CR^W$ and $CR^Y$, respectively; and

Z is $NR^Z$, and the compounds are imidazolium salts.

11. The method of claim 7 comprising administering an effective amount of a compound of the formula I, wherein:

W is $CR^W$ and Y is N;

Z is S and the compounds are [1,2,4]-thiadiazolium salts; and $R^W$ is hydrogen, alkyl, aryloxy, arylthio, amino, alkylamino, dialkylamino, fluoroalkyl, perfluoroaryl, or hydroxyalkyl.

12. The method of claim 6 comprising administering an effective amount of a compound of the formula I, wherein $Q=$—$CH_2$—.

13. The method of claim 12 comprising administering an effective amount of a compound of the formula I, wherein:

W is N and Y is $CR^Y$;

Z is O and the compounds are [1,3,4]-oxadiazolium salts; and $R^Y$ is hydrogen, alkyl, aryloxy, arylthio, amino, alkylamino, dialkylamino, fluoroalkyl, perfluoroaryl, or hydroxyalkyl.

14. The method of claim 12 comprising administering an effective amount of a compound of the formula I, $Q=$—$CH_2$— wherein:

W is N and Y is $CR^Y$;

Z is $NR^Z$ and the compounds are [1,2,4]-triazolium salts; and $R^Y$ is hydrogen, alkyl, aryloxy, arylthio, amino, alkylamino, dialkylamino, fluoroalkyl, perfluoroaryl, or hydroxyalkyl.

15. The method of claim 12 comprising administering an effective amount of a compound of the formula I, Q=—$CH_2$—
wherein:

W and Y are $CR^W$ and $CR^Y$, respectively; and

Z is $NR^Z$, and the compounds are imidazolium salts.

16. The method of claim 12 comprising administering an effective amount of a compound of the formula I, wherein:

W is $CR^W$ and Y is N;

Z is S and the compounds are [1,2,4]-thiadiazolium salts; and $R^W$ is hydrogen, alkyl, aryloxy, arylthio, amino, alkylamino, dialkylamino, fluoroalkyl, perfluoroaryl, or hydroxyalkyl.

17. The method of claim 1, wherein the administered compound is of formula I, wherein Q=—(CO)—$CH_2$— and:

W and Y are $C(CH_3)$;

Z is S;

$R_1$=R2=R3=$CH_3$ or $R_1$=$R_3$=$CH_3$, $R_2$=H; and $R_4$ is H or $CH_3$.

18. The method of claim 1, wherein the administered compound is of formula I, wherein Q=—(CO)—$CH_2$— and:

W is N, Y is $C(CH_3)$;

Z is S;

$R_1$=$R_2$=$R_3$=$CH_3$ or $R_1$=$R_3$=$CH_3$, $R_2$=H; and $R_4$ is H or $CH_3$.

19. The method of claim 1, wherein the administered compound is of formula I, wherein Q=—(CO)—$CH_2$— and:

W is N and Y is $C(CH_3)$;

Z is N—$C_6H_5$;

$R_1$=$R_3$=$CH_3$, $R_2$=H or $R_1$=$R_2$=$R_3$=CH3; and $R_4$ is H.

20. The method of claim 1, wherein the administered compound is of formula I, wherein Q=—(CO)—$CH_2$— and:

W is N and Y is $C(CH_3)$;

Z is N—$CH_3$;

$R_1$=$R_2$=$CH_3$, $R_3$=H; and $R_4$ is H.

21. The method of claim 1, wherein the administered compound is of formula I, wherein Q=—$CH_2$— and:

W and Y are $C(CH_3)$;

Z is S;

$R_1$=$R_2$=$R_3$=$CH_3$ or R=$R_3$=$CH_3$, $R_2$=H; and $R_4$ is H or $CH_3$.

22. The method of claim 1, wherein the administered compound is of formula I, Q=—$CH_2$— and:

W is N, Y is $C(CH_3)$;

Z is S;

$R_1$=$R_2$=$R_3$=$CH_3$ or $R_1$=$R_3$=$CH_3$, $R_2$=H; and $R_4$ is H or $CH_3$.

23. The method of claim 1, wherein the administered compound is of formula I, wherein Q=—$CH_2$— and:

W is N and Y is $C(CH_3)$;

Z is N—$C_6H_5$;

$R_1$=$R_2$=$R_3$=$CH_3$ or $R_1$=$R_3$=$CH_3$, $R_2$=H;

$R_4$ is H.

24. The method of claim 1, wherein reduced vascular compliance is treated in the subject.

25. The method of claim 1, wherein elevated pulse pressure is treated in the subject.

26. The method of claim 1, wherein hypertension is treated in the subject.

27. The method of claim 26, wherein the hypertension is isolated systolic hypertension.

28. The method of claim 1, wherein left ventricular hypertrophy is treated in the subject.

* * * * *